United States Patent
Zielinski et al.

(10) Patent No.: US 8,483,826 B2
(45) Date of Patent: Jul. 9, 2013

(54) DEACTIVATION OF INTERMITTENT PACING THERAPY

(75) Inventors: John R. Zielinski, Eagan, MN (US); Shantha Arcot-Krishnamurthy, Vadnais Heights, MN (US); Joseph M. Pastore, Mentor, OH (US); Jeffrey E. Stahmann, Ramsey, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1149 days.

(21) Appl. No.: 12/405,990

(22) Filed: Mar. 17, 2009

(65) Prior Publication Data

US 2009/0234401 A1 Sep. 17, 2009

Related U.S. Application Data

(60) Provisional application No. 61/037,270, filed on Mar. 17, 2008.

(51) Int. Cl.
*A61N 1/00* (2006.01)

(52) U.S. Cl.
USPC ........... 607/9; 607/4; 607/15; 607/17; 607/18

(58) Field of Classification Search
USPC ................ 607/4–38, 119–132; 600/373–375, 600/449–450, 481–503, 508–528
See application file for complete search history.

(56) References Cited

U.S. PATENT DOCUMENTS

| 4,587,975 A | 5/1986 | Salo et al. |
| 4,730,619 A | 3/1988 | Koning et al. |
| 4,773,401 A | 9/1988 | Citak et al. |
| 4,834,710 A | 5/1989 | Fleck |
| 4,872,459 A | 10/1989 | Pless et al. |
| 4,919,133 A | 4/1990 | Chiang |

(Continued)

FOREIGN PATENT DOCUMENTS

| EP | 1437159 A1 | 7/2004 |
| WO | WO-9518649 A1 | 7/1995 |

(Continued)

OTHER PUBLICATIONS

"International Application Serial No. PCT/US2009/001674, International Search Report mailed Nov. 5, 2009", 5 pgs.

(Continued)

*Primary Examiner* — Niketa Patel
*Assistant Examiner* — Lindsey G Hankins
(74) *Attorney, Agent, or Firm* — Schwegman Lundberg & Woessner, P.A.

(57) ABSTRACT

This document discusses, among other things, an apparatus comprising an implantable cardiac depolarization sensing circuit, an electrical stimulation circuit, and a pacing mode controller. The pacing mode controller is configured to deliver pacing therapy according to a first pacing mode that is a normal operating mode, and to deliver pacing therapy according to second and third pacing modes. The second and third pacing modes increase mechanical stress on at least a particular portion of the ventricle as compared to the pacing therapy delivered during the first pacing mode. The pacing mode controller alternates between the second and third pacing modes when pacing is changed from the normal operating mode to a stress augmentation mode. The pacing mode controller suspends the change from the normal operating mode to the stress augmentation mode when a condition to prevent the change is detected.

28 Claims, 5 Drawing Sheets

U.S. PATENT DOCUMENTS

| | | |
|---|---|---|
| 5,007,427 A | 4/1991 | Suzuki et al. |
| 5,072,458 A | 12/1991 | Suzuki |
| 5,111,818 A | 5/1992 | Suzuki et al. |
| 5,135,004 A | 8/1992 | Adams et al. |
| 5,178,149 A | 1/1993 | Imburgia et al. |
| 5,184,615 A | 2/1993 | Nappholz et al. |
| 5,203,326 A | 4/1993 | Collins |
| 5,282,840 A | 2/1994 | Hudrlik et al. |
| 5,313,953 A | 5/1994 | Yomtov et al. |
| 5,376,106 A | 12/1994 | Stahmann et al. |
| 5,447,529 A | 9/1995 | Marchlinski et al. |
| 5,484,419 A | 1/1996 | Fleck |
| 5,531,768 A | 7/1996 | Alferness |
| 5,588,432 A | 12/1996 | Crowley |
| 5,755,671 A | 5/1998 | Albrecht et al. |
| 5,919,209 A | 7/1999 | Schouten |
| 6,076,015 A | 6/2000 | Hartley et al. |
| 6,108,577 A | 8/2000 | Benser |
| 6,115,628 A | 9/2000 | Stadler et al. |
| 6,233,486 B1 | 5/2001 | Ekwall et al. |
| 6,238,422 B1 | 5/2001 | Oort |
| 6,256,538 B1 | 7/2001 | Ekwall |
| 6,272,379 B1 | 8/2001 | Fischell et al. |
| 6,314,323 B1 | 11/2001 | Ekwall et al. |
| 6,368,284 B1 | 4/2002 | Bardy |
| 6,408,208 B1 | 6/2002 | Sun |
| 6,411,845 B1 | 6/2002 | Mower |
| 6,477,402 B1 | 11/2002 | Lynch et al. |
| 6,493,579 B1 | 12/2002 | Gilkerson et al. |
| 6,569,145 B1 | 5/2003 | Shmulewitz et al. |
| 6,584,362 B1 | 6/2003 | Scheiner et al. |
| 6,604,000 B2 | 8/2003 | Lu |
| 6,610,713 B2 | 8/2003 | Tracey |
| 6,628,988 B2 | 9/2003 | Kramer et al. |
| 6,711,436 B1 | 3/2004 | Duhaylongsod |
| 6,763,267 B2 | 7/2004 | Ding |
| 6,827,690 B2 | 12/2004 | Bardy |
| 6,838,471 B2 | 1/2005 | Tracey |
| 6,845,267 B2 | 1/2005 | Harrison et al. |
| 6,865,420 B1 | 3/2005 | Kroll |
| 6,882,883 B2 | 4/2005 | Condie et al. |
| 6,889,081 B2 | 5/2005 | Hsu |
| 6,892,095 B2 | 5/2005 | Salo |
| 6,913,577 B2 | 7/2005 | Bardy |
| 6,937,899 B2 | 8/2005 | Sheldon et al. |
| 6,950,701 B2 | 9/2005 | Begemann et al. |
| 6,957,104 B2 | 10/2005 | Wagner |
| 6,965,797 B2 | 11/2005 | Pastore et al. |
| 6,973,349 B2 | 12/2005 | Salo |
| 7,010,345 B2 | 3/2006 | Hill et al. |
| 7,025,730 B2 | 4/2006 | Cho et al. |
| 7,039,462 B2 | 5/2006 | Pastore et al. |
| 7,062,314 B2 | 6/2006 | Zhu et al. |
| 7,069,070 B2 | 6/2006 | Carlson et al. |
| 7,072,711 B2 | 7/2006 | Girouard et al. |
| 7,215,992 B2 | 5/2007 | Stahmann et al. |
| 7,215,997 B2 | 5/2007 | Yu et al. |
| 7,277,761 B2 | 10/2007 | Shelchuk |
| 7,295,874 B2 | 11/2007 | Prinzen et al. |
| 7,299,087 B2 | 11/2007 | Bardy |
| 7,333,854 B1 | 2/2008 | Brewer et al. |
| 7,340,303 B2 | 3/2008 | Zhu |
| 7,364,547 B2 | 4/2008 | Stahmann et al. |
| 7,366,568 B2 | 4/2008 | Pastore et al. |
| 7,437,191 B2 | 10/2008 | Pastore et al. |
| 7,460,906 B2 | 12/2008 | Libbus |
| 7,479,112 B2 | 1/2009 | Sweeney et al. |
| 7,486,991 B2 | 2/2009 | Libbus et al. |
| 7,668,594 B2 | 2/2010 | Brockway et al. |
| 2002/0026222 A1 | 2/2002 | Schauerte et al. |
| 2002/0042632 A1 | 4/2002 | Iaizzo et al. |
| 2002/0072777 A1 | 6/2002 | Lu |
| 2002/0123772 A1 | 9/2002 | Sun et al. |
| 2002/0128563 A1 | 9/2002 | Carlson et al. |
| 2003/0004549 A1 | 1/2003 | Hill et al. |
| 2003/0009189 A1 | 1/2003 | Gilson et al. |
| 2003/0045908 A1 | 3/2003 | Condie et al. |
| 2003/0060854 A1 | 3/2003 | Zhu |
| 2003/0105493 A1 | 6/2003 | Salo |
| 2003/0120315 A1 | 6/2003 | Spinelli et al. |
| 2003/0139778 A1 | 7/2003 | Fischell et al. |
| 2003/0195572 A1 | 10/2003 | Bocek et al. |
| 2003/0199956 A1 | 10/2003 | Struble et al. |
| 2003/0233130 A1 | 12/2003 | Padmanabhan et al. |
| 2003/0233132 A1 | 12/2003 | Pastore et al. |
| 2004/0015081 A1 | 1/2004 | Kramer et al. |
| 2004/0038947 A1 | 2/2004 | Wink et al. |
| 2004/0088015 A1 | 5/2004 | Casavant et al. |
| 2004/0088017 A1 | 5/2004 | Sharma et al. |
| 2004/0102815 A1 | 5/2004 | Balczewski et al. |
| 2004/0104688 A1 | 6/2004 | Takeuchi et al. |
| 2004/0106960 A1 | 6/2004 | Siejko et al. |
| 2004/0133247 A1 | 7/2004 | Stahmann et al. |
| 2004/0230240 A1 | 11/2004 | Sun et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0043675 A1 | 2/2005 | Pastore et al. |
| 2005/0075673 A1 | 4/2005 | Warkentin et al. |
| 2005/0090719 A1 | 4/2005 | Scheiner et al. |
| 2005/0096705 A1 | 5/2005 | Pastore et al. |
| 2005/0096706 A1 | 5/2005 | Salo |
| 2005/0137631 A1 | 6/2005 | Yu et al. |
| 2005/0143779 A1 | 6/2005 | Libbus |
| 2005/0149129 A1 | 7/2005 | Libbus et al. |
| 2005/0171589 A1 | 8/2005 | Lau et al. |
| 2005/0197674 A1 | 9/2005 | McCabe et al. |
| 2005/0261741 A1 | 11/2005 | Libbus et al. |
| 2005/0288721 A1 | 12/2005 | Girouard et al. |
| 2006/0030892 A1 | 2/2006 | Kadhiresan et al. |
| 2006/0116593 A1 | 6/2006 | Zhang et al. |
| 2006/0136049 A1 | 6/2006 | Rojo |
| 2006/0149326 A1 | 7/2006 | Prinzen et al. |
| 2006/0195038 A1 | 8/2006 | Carlson et al. |
| 2006/0206158 A1 | 9/2006 | Wu et al. |
| 2006/0241704 A1 | 10/2006 | Shuros et al. |
| 2006/0247686 A1 | 11/2006 | Girouard et al. |
| 2006/0247700 A1 | 11/2006 | Jackson |
| 2006/0253156 A1* | 11/2006 | Pastore et al. ..................... 607/9 |
| 2006/0259087 A1 | 11/2006 | Baynham et al. |
| 2006/0259088 A1 | 11/2006 | Pastore et al. |
| 2006/0282000 A1 | 12/2006 | Zhang et al. |
| 2006/0287684 A1 | 12/2006 | Baynham et al. |
| 2007/0021789 A1 | 1/2007 | Pastore et al. |
| 2007/0038261 A1 | 2/2007 | Kieval et al. |
| 2007/0043393 A1 | 2/2007 | Brockway et al. |
| 2007/0060972 A1 | 3/2007 | Kieval et al. |
| 2007/0142871 A1 | 6/2007 | Libbus et al. |
| 2007/0150005 A1 | 6/2007 | Sih et al. |
| 2007/0162081 A1 | 7/2007 | Yu et al. |
| 2007/0179392 A1 | 8/2007 | Zhang |
| 2007/0239218 A1 | 10/2007 | Carlson et al. |
| 2007/0260284 A1 | 11/2007 | Pastore et al. |
| 2007/0282380 A1 | 12/2007 | Brooke et al. |
| 2007/0299356 A1 | 12/2007 | Wariar et al. |
| 2008/0015659 A1 | 1/2008 | Zhang et al. |
| 2008/0021507 A1 | 1/2008 | Libbus et al. |
| 2008/0027495 A1 | 1/2008 | Prinzen et al. |
| 2008/0058661 A1 | 3/2008 | Bardy |
| 2008/0058881 A1 | 3/2008 | Wagner et al. |
| 2008/0077187 A1 | 3/2008 | Levin et al. |
| 2008/0081354 A1 | 4/2008 | Qu et al. |
| 2008/0082135 A1 | 4/2008 | Arcot et al. |
| 2008/0091138 A1 | 4/2008 | Pastore et al. |
| 2008/0132972 A1 | 6/2008 | Shuros et al. |
| 2008/0140141 A1 | 6/2008 | Ben-David et al. |
| 2008/0177156 A1 | 7/2008 | Zhang et al. |
| 2008/0177191 A1 | 7/2008 | Patangay et al. |
| 2008/0177194 A1 | 7/2008 | Zhang et al. |
| 2008/0215105 A1 | 9/2008 | Pastore et al. |
| 2008/0221636 A1 | 9/2008 | Pastore et al. |
| 2008/0234772 A1 | 9/2008 | Shuros et al. |
| 2008/0234774 A1 | 9/2008 | Baynham et al. |
| 2009/0025459 A1 | 1/2009 | Zhang et al. |
| 2009/0043348 A1 | 2/2009 | Pastore et al. |
| 2009/0048641 A1 | 2/2009 | Libbus |
| 2009/0082781 A1 | 3/2009 | Tran et al. |

| | | | |
|---|---|---|---|
| 2009/0192560 | A1 | 7/2009 | Arcot-Krishnamurthy et al. |
| 2009/0234416 | A1 | 9/2009 | Zielinski et al. |
| 2010/0121391 | A1 | 5/2010 | Brockway et al. |

FOREIGN PATENT DOCUMENTS

| | | |
|---|---|---|
| WO | WO-0128625 | 4/2001 |
| WO | WO-0176689 A2 | 10/2001 |
| WO | WO-2004058326 A2 | 7/2004 |
| WO | WO-2005/030325 A1 | 4/2005 |
| WO | WO-2005042091 A1 | 5/2005 |
| WO | WO-2006074189 A1 | 7/2006 |
| WO | WO-2006079010 A1 | 7/2006 |
| WO | WO-2006/124636 A2 | 11/2006 |
| WO | WO-2006115693 A2 | 11/2006 |
| WO | WO-2006115693 A3 | 11/2006 |
| WO | WO-2006121842 A2 | 11/2006 |
| WO | WO-2006124729 A2 | 11/2006 |
| WO | WO-2007078410 A1 | 7/2007 |
| WO | WO-2007/130774 A2 | 11/2007 |
| WO | WO-2007133962 A2 | 11/2007 |
| WO | WO-2009097118 A1 | 8/2009 |
| WO | WO-2009/117086 A2 | 9/2009 |

OTHER PUBLICATIONS

"International Application Serial No. PCT/US2009/001674, Written Opinion mailed Nov. 5, 2009", 8 pgs.

"U.S. Appl. No. 11/030,575, Non-Final Office Action mailed Jul. 26, 2006", 10 pgs.

"U.S. Appl. No. 11/030,575, Response filed Oct. 26, 2006 to Non Final Office Action mailed Jul. 26, 2006 ", 8 pgs.

"U.S. Appl. No. 11/151,015, Non-Final Office Action mailed May 21, 2007", 10 pgs.

"U.S. Appl. No. 11/151,015, Response filed Aug. 21, 2007 to Non-Final Office Action mailed May 21, 2007", 9 pgs.

"U.S. Appl. No. 11/207,251, Final Office Action mailed Feb. 3, 2009", 9 pgs.

"U.S. Appl. No. 11/207,251, Non-Final Office Action mailed Jun. 27, 2008", 8 pgs.

"U.S. Appl. No. 11/207,251, Notice of Allowance mailed May 28, 2009", 4 pgs.

"U.S. Appl. No. 11/207,251, Notice of Allowance mailed Sep. 28, 2009", 4 pgs.

"U.S. Appl. No. 11/207,251, Response filed Apr. 7, 2009 to Final Office Action mailed Feb. 3, 2009", 11 pgs.

"U.S. Appl. No. 11/207,251, Response filed Sep. 29, 2008 to Non Final Office Action mailed Jun. 27, 2008", 14 pgs.

"U.S. Appl. No. 11/318,263, Non-Final Office Action mailed Aug. 20, 2008", 9 pgs.

"U.S. Appl. No. 11/318,263, Response filed May 22, 2008 to Restriction Requirement mailed Apr. 23, 2008", 10 pgs.

"U.S. Appl. No. 11/318,263, Response filed Nov. 20, 2008 to Non Final Office Action mailed Aug. 20, 2008", 12 pgs.

"U.S. Appl. No. 12/361,353, Final Office Action Mailed Mar. 5, 2012", 12 pgs.

"U.S. Appl. No. 12/361,353, Non-Final Office Action mailed Oct. 5, 2011", 13 pgs.

"U.S. Appl. No. 12/361,353, Response filed Jan. 4, 2012 to Non Final Office Action mailed Oct. 5, 2011", 15 pgs.

"U.S. Appl. No. 12/401,194, Non-Final Office Action mailed Jul. 21, 2011", 11 pgs.

"U.S. Appl. No. 12/401,194, Notice of Allowance mailed Nov. 1, 2011", 11 pgs.

"U.S. Appl. No. 12/401,194, Response filed Jun. 6, 2011 to Restriction Requirement mailed May 4, 2011", 12 pgs.

"U.S. Appl. No. 12/401,194, Restriction Requirement mailed May 4, 2011", 7 pgs.

"U.S. Appl. No. 12/689,016, Non-Final Office Action mailed Dec. 22, 2011", 11 pgs.

"Australian Application Serial No. 2009209397, First Examiner Report mailed Sep. 1, 2011", 4 pgs.

"International Application Serial No. PCT/US2006/000125, International Search Report and Written Opinion mailed May 11, 2006", 12 pgs.

"International Application Serial No. PCT/US2006/017384, International Search Report and Written Opinion mailed Jan. 23, 2007", 12 pgs.

"International Application Serial No. PCT/US2007/068217, International Search Report mailed Oct. 30, 2007", 5 pgs.

"International Application Serial No. PCT/US2007/068217, Written Opinion mailed Oct. 30, 2007", 8 pgs.

"International Application Serial No. PCT/US2009/000552, International Search Report mailed Apr. 5, 2009", 4 pgs.

"International Application Serial No. PCT/US2009/000552, Written Opinion mailed Apr. 5, 2009", 9 pgs.

Andersen, H, et al., "Long-term follow-up of patients from a randomised trial of atrial versus ventricular pacing for sick-sinus syndrome", Lancet, 350(9086), (Oct. 25, 1997), 1210-6.

Benchimol, A, et al., "Cardiac hemodynamics during stimulation of the right atrium, right ventricle, and left ventricle in normal and abnormal hearts", Circulation, 33(6), (Jun. 1966), 933-44.

Leclercq, C, et al., "Hemodynamic importance of preserving the normal sequence of ventricular activation in permanent cardiac pacing", Am Heart J., 129(6), (Jun. 1995), 1133-41.

Loukogeorgakis, S. P., et al., "Remote ischemic preconditioning provides early and late protection against endothelial ischemia-reperfusion injury in humans: role of the autonomic nervous system.", J Am Coll Cardiol., 46(3), (Aug. 2, 2005), 450-6.

Meier, B., et al., "Coronary Pacing During Percutaneous Transluminal Coronary Angioplasty", Circulation, 71(3), (Mar. 1985), 557-561.

Rosa, A., et al., "Ectopic Pacing at Physiological Rate Improves Postanoxic Recovery of the Developing Heart", Am. J. Physiol.—Heart Circ. Physiol., 284, (2003), H2384-H2392.

Rosenqvist, M, et al., "The effect of ventricular activation sequence on cardiac performance during pacing", Pacing and Electrophysiology, 19(9), (1996), 1279-1286.

Tsang, A., et al., "Postconditioning: a form of "modified reperfusion" protects the myocardium by activating the phosphatidylinositol 3-kinase-Akt pathway", Circ Res., 95(3), Epub Jul. 8, 2004 (Aug. 6, 2004), 230-2.

Vanagt, W. Y. R., et al., "Ventricular Pacing for Improving Myocardial Tolerance to Ischemia", Progress Report on Project Guidant-CARIM, (Oct. 2003), 1-25.

Wu, Zhong-Kai, et al., "Ischemic preconditioning suppresses ventricular tachyarrhythmias after myocardial revascularization", Circulation, 106(24), (Dec. 10, 2002), 3091-3096.

Yang, S. M., et al., "Multiple, brief coronary occlusions during early reperfusion protect rabbit hearts by targeting cell signaling pathways", Journal of the American College of Cardiology, 44(5), (Sep. 1, 2004), 1103-1110.

Zhao, et al., "Inhibition of myocardial injury by ischemic postconditioning during reperfusion: comparison with ischemic preconditioning", Am J Physiol Heart Circ Physiol, 285(2), (Aug. 2003), H579-H588.

"U.S. Appl. No. 12/361,353, Examiner Interview Summary mailed May 2, 2012", 3 pgs.

"U.S. Appl. No. 12/361,353, Response filed May 9, 2012 to Final Office Action mailed Mar. 5, 2012", 16 pgs.

* cited by examiner

DEACTIVATION OF INTERMITTENT PACING THERAPY

RELATED APPLICATIONS

This application claims the benefit under 35 U.S.C. 119(e) of U.S. Provisional Patent Application Ser. No. 61/037,270, filed on Mar. 17, 2008, which is incorporated herein by reference in it entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. Some IMDs derive measurements of hemodynamic parameters related to chamber filling and contractions from electrical signals provided by sensors. Sometimes patients who receive IMDs have experienced heart failure (HF) decompensation or other events associated with worsening HF. Some patients have experienced repeated HF decompensations. Symptoms associated with worsening HF include pulmonary and/or peripheral edema, dilated cardiomyopathy, or ventricular dilatation. Early attention to signs and symptoms of HF decompensation is needed for the health of the patient and allows early initiation of treatment.

OVERVIEW

This document relates generally to apparatuses, systems, and methods to provide electrical pacing therapy to a patient or subject. In example 1, an apparatus includes an implantable cardiac depolarization sensing circuit, an electrical stimulation circuit, and a pacing mode controller. The cardiac depolarization sensing circuit is configured to obtain a sensed depolarization signal from a ventricle and the electrical stimulation circuit is configured to provide pacing electrical stimulation energy to an implantable ventricular electrode. The pacing mode controller is configured to deliver pacing therapy according to a first pacing mode that is a normal operating mode, and to deliver pacing therapy according to a second pacing mode and a third pacing mode different from the second pacing mode. The second and third pacing modes increase mechanical stress on at least a particular portion of the ventricle as compared to the pacing therapy delivered during the first pacing mode. The pacing mode controller is configured to alternate between the second and third pacing modes when pacing is changed from the normal operating mode to a stress augmentation mode, and suspend a change from the normal operating mode to the stress augmentation mode when a condition to prevent the change is detected.

In example 2, the pacing mode controller of example 1 is optionally configured to retry the change to the stress augmentation mode after suspending the change from the normal operating mode. In example 3, the pacing mode controller of examples 1 and 2 optionally includes a timer circuit, and the pacing mode controller is configured to retry the change from the normal operating mode to the stress augmentation mode after a programmable time duration.

In example 4, the pacing mode controller of examples 1-3 optionally includes a counter circuit, and the pacing mode controller is configured to retry the change from the normal operating mode to the stress augmentation mode for a programmable number of retry attempts before deactivating the stress augmentation mode. In example 5, the pacing mode controller of examples 1-4 is optionally configured to retry the change from the normal operating mode to the stress augmentation mode when the condition preventing the change is no longer detected.

In example 6, the pacing mode controller of examples 1-5 is optionally configured to suspend the change to the stress augmentation mode when delivering atrial tachyarrhythmia response pacing therapy in the first pacing mode.

In example 7, the apparatus of claims 1-6 optionally includes an electrical high-energy shock stimulation circuit, communicatively coupled to the pacing mode controller, configured to provide at least one of cardioversion or defibrillation electrical stimulation energy to at least one implantable electrode, and the pacing mode controller of the examples is optionally configured to suspend the change to the stress augmentation mode during delivery of the cardioversion or defibrillation electrical stimulation energy.

In example 8, the apparatus of examples 1-7 optionally includes an electrical neural stimulation circuit, communicatively coupled to the pacing mode controller, configured to provide electrical neural stimulation energy to at least one implantable electrode, and the pacing mode controller of the examples is optionally configured to suspend the change to the stress augmentation mode during delivery of the electrical neural stimulation energy.

In example 9, the apparatus of examples 1-8 optionally includes a preventing condition detector, communicatively coupled to the pacing mode controller and the cardiac depolarization sensing circuit, configured to determine a heart rate using the sensed depolarization signal and to detect when the heart rate of a patient exceeds a heart rate threshold value. The pacing mode controller of the examples is optionally configured to suspend the change to the stress augmentation mode when the preventing condition detector detects the heart rate exceeds the heart rate threshold value.

In example 10, the apparatus of examples 1-9 optionally includes an activity sensor circuit to produce an activity sensor signal representative of activity of a patient, and a preventing condition detector, communicatively coupled to the pacing mode controller and the activity sensor circuit, configured to detect from the activity sensor signal when an activity level of the patient exceeds an activity level threshold value. The pacing mode controller of the examples is optionally configured to suspend the change to the stress augmentation mode when the activity level of the patient exceeds the activity level threshold value.

In example 11, the apparatus of examples 1-10 optionally includes a signal analyzer circuit communicatively coupled to the cardiac depolarization sensing circuit, which is configured to execute a scheduled measurement using the sensed depolarization signal, and the pacing mode controller of the examples is optionally configured to suspend the change to the stress augmentation mode during the scheduled measurement. In example 12, the signal analyzer circuit of examples 1-11 is optionally configured to execute a diagnostic measurement using the sensed depolarization signal, and the pacing mode controller is optionally configured to suspend the change to the stress augmentation mode during the diagnostic measurement.

In example 13, the apparatus of examples 1-12 optionally includes an implantable impedance sensor circuit configured to provide a sensed cardiac impedance signal, and the pacing mode controller is optionally configured to suspend the change to the stress augmentation mode during the diagnostic measurement.

In example 14, the signal analyzer circuit of examples 1-13 is optionally configured to detect, using the sensed depolarization signal, electrical energy applied by a second separate device as part of a diagnostic measurement. The pacing mode controller of the examples is optionally configured to suspend the change to the stress augmentation mode when the preventing condition detector detects the applied electrical energy.

In example 15, the apparatus of examples 1-14 optionally includes a magnetic field sensor circuit communicatively coupled to the pacing mode controller, and the pacing mode controller is optionally configured to suspend the change to the stress augmentation mode when the magnetic field sensor circuit detects a magnetic field.

In example 16, the apparatus of examples 1-15 optionally includes a respiration sensor circuit configured to produce a respiration sensor signal representative of respiration of a patient, and a preventing condition detector communicatively coupled to the pacing mode controller and the respiration sensor circuit. The preventing condition detector is configured to detect, using the respiration sensor signal, an episode of at least one of apnea, hypopnea, or hyperventilation. The pacing mode controller of the examples is optionally configured to suspend the change to the stress augmentation mode during the episode.

In example 17, a method includes delivering pacing therapy using an implantable device according to a first pacing mode that is a normal operating mode, and delivering pacing therapy according to a second pacing mode and a third pacing mode that is different from the second pacing mode. The second pacing mode and the third pacing mode increase mechanical stress on at least a particular portion of the ventricle as compared to the pacing therapy delivered during the first pacing mode. The method also includes alternating between the second and third pacing modes when changed from the normal operating mode to a stress augmentation mode, and suspending a change to the stress augmentation mode when a condition to prevent the change is present.

In example 18, the method of example 17 optionally includes retrying the change from the normal operating mode to the stress augmentation mode after suspending the change to the stress augmentation mode. In example 19, the method of examples 17 and 18 optionally includes retrying the change from the normal operating mode to the stress augmentation mode after a programmable time duration.

In example 20, the method of examples 17-19 optionally includes retrying the change from the normal operating mode to the stress augmentation mode for a programmable number of retry attempts before deactivating the stress augmentation mode. In example 21, the method of examples 17-20 optionally includes retrying the change from the normal operating mode to the stress augmentation mode after the implantable device determines the condition preventing the change is no longer present.

In example 22, the suspending a change to the stress augmentation mode of examples 17-21 optionally includes suspending the change during delivery of a different higher priority therapy. In example 23, the suspending the change of examples 17-22 optionally includes the suspending the change during at least one of: delivering pacing therapy according to an atrial tachyarrhythmia response in the first pacing mode, delivering defibrillation therapy, delivering cardioversion therapy, or delivering neural stimulation therapy.

In example 24, the suspending a change to the stress augmentation mode of examples 17-23 optionally includes suspending the change to the stress augmentation mode when the implantable device detects a patient is exercising. In example 25, the suspending a change to the stress augmentation mode of examples 17-24 optionally includes suspending a change to the stress augmentation mode until after a scheduled measurement is completed by the implantable device.

In example 26, the suspending a change to the stress augmentation mode of examples 17-25 optionally includes suspending the change when the implantable device determines a patient diagnostic measurement is being made. In example 27, the suspending a change to the stress augmentation mode optionally includes suspending the change to the stress augmentation mode when the implantable device detects a presence of a magnetic field.

In example 28, the suspending a change to the stress augmentation mode in the method of examples 17-27 optionally includes suspending the change to the stress augmentation mode when the implantable device detects an indication of at least one of: apnea, hypopnea, or hyperventilation.

In example 29, a method includes delivering pacing therapy according to a first pacing mode using an implantable device, wherein the first pacing mode is a normal operating mode, and determining if pacing according to a stress augmentation mode is scheduled. The stress augmentation mode increases mechanical stress on at least a particular portion of the ventricle as compared to the pacing therapy delivered during the first pacing mode. The method also includes rescheduling a change to the stress augmentation mode when a condition to prevent the change is present. Otherwise, the method includes delivering pacing therapy according to a second pacing mode while in the stress augmentation mode, delivering pacing therapy according to a third pacing mode different from the second pacing mode while in the stress augmentation mode, and alternating between the second and third pacing modes, when pacing is changed from the normal operating mode to the stress augmentation mode.

In example 30, the rescheduling a change to the stress augmentation mode of example 20 optionally includes retrying includes retrying the change from the normal operating mode to the stress augmentation mode after a programmable time duration.

In example 31, the rescheduling a change to the stress augmentation mode of examples 29 and 30 optionally includes retrying the change from the normal operating mode to the stress augmentation mode for a programmable number of retry attempts before deactivating the stress augmentation mode.

In example 32, the rescheduling a change to the stress augmentation mode of examples 29-31 optionally includes retrying the change from the normal operating mode to the stress augmentation mode after the implantable device determines the condition to prevent the change is no longer present.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

Figure 1:
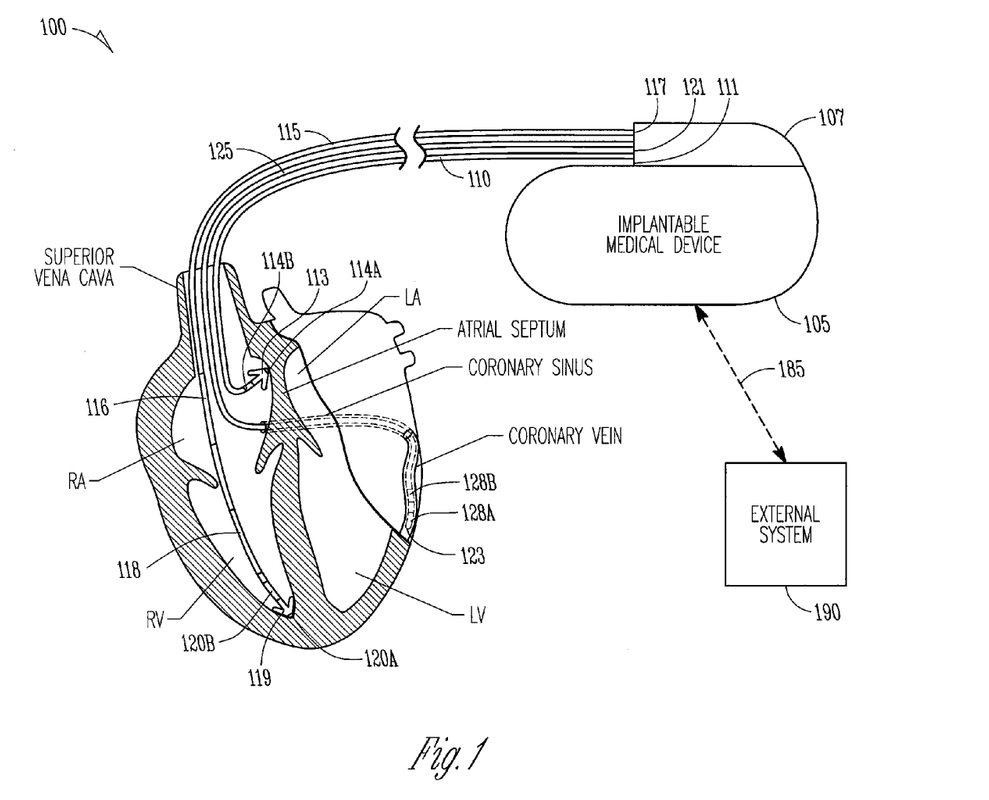
FIG. 1 is an illustration of portions of a system that uses an IMD.

FIG. 1 is an illustration of portions of a system 100 that uses an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

The IMDs may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

As discussed above, symptoms associated with worsening HF may include progressive ventricular dilatation, or a decline in ejection fraction. Occasionally causing dyssynchrony of ventricular contractions may prevent progressive ventricular dilatation. This dyssynchrony may be provided by an intermittent pacing therapy using an IMD. The intermittent pacing therapy is designed to increase ventricular dyssynchrony to cause stress in regional areas of the myocardial wall. The stress is caused in regions that are activated later than others. Providing this intermittent regional stress may halt progression of ventricular dilatation.

Figure 2:
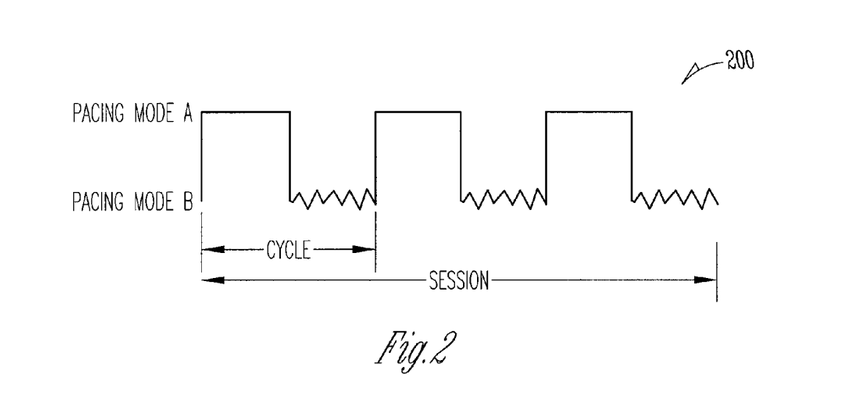
FIG. 2 is an illustration of a timing diagram of an example of intermittent pacing therapy provided by an IMD.

FIG. 2 is an illustration of a timing diagram 200 of an example of intermittent pacing therapy (IPT) provided by an IMD. The timing diagram 200 shows an intermittent pacing therapy session. Prior to and after the intermittent pacing session, the IMD provides pacing therapy in a normal operating mode that allows for regular depolarizations to occur in the heart chamber (e.g., the NASPE/BPEG-defined DDD pacing mode). The intermittent pacing session includes three cycles of alternating Pacing Mode A with Pacing Mode B. Pacing mode B may be different from pacing mode A. The alternating of Pacing Mode A with Pacing Mode B increases mechanical stress on at least a particular portion of a ventricle as compared to the pacing therapy delivered during the normal operating mode. This intermittent pacing therapy can be referred to as a stress augmentation mode and is designed to provide control over the progression of ventricular dilatation.

Figure 3:
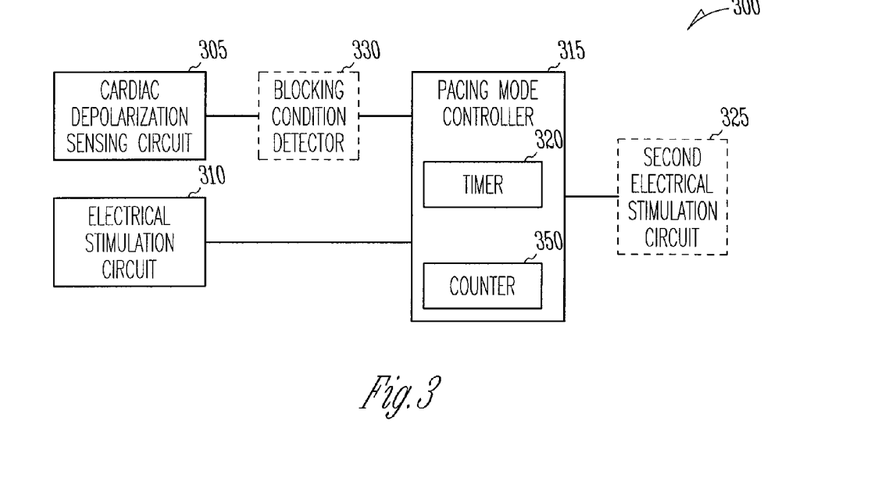
FIG. 3 is a block diagram of portions of an example of an IMD to provide intermittent pacing therapy in a stress augmentation mode.

FIG. 3 is a block diagram of portions of an example of an IMD 300 to provide intermittent pacing therapy in a stress augmentation mode. The IMD 300 includes at least one implantable cardiac depolarization sensing circuit 305, an electrical stimulation circuit 310, and a pacing mode controller 315. The cardiac depolarization sensing circuit 305 obtains a sensed depolarization signal from a ventricle such as by using a sense amplifier circuit for example. The electrical stimulation circuit provides pacing electrical stimulation energy to at least one implantable ventricular electrode.

The pacing mode controller 315 may include a digital signal processor, application specific integrated circuit (ASIC), microprocessor, or other type of processor, interpreting or executing instructions in software or firmware. The pacing mode controller 315 may include any combination of hardware, firmware, or software. In some examples, the pacing mode controller 315 may include a state machine or sequencer that is implemented in hardware circuits. The pacing mode controller 315 may include one or more circuits to perform the functions described herein. A circuit may include software, hardware, firmware or any combination thereof. For example, the circuit may include instructions in software executing on the pacing mode controller 315. Multiple functions may be performed by one or more circuits.

The pacing mode controller 315 is communicatively coupled to the cardiac depolarization sensing circuit 305 and the electrical stimulation circuit 310 (e.g., the pacing mode controller 315 is able to communicate signals with the cardiac depolarization sensing circuit 305 and the electrical stimulation circuit 310 even though there may be intervening circuitry coupled between them). The pacing mode controller 315 delivers pacing therapy (via the cardiac depolarization sensing circuit 305 and the electrical stimulation circuit 310) according to a first mode that is a normal operating mode. The pacing mode controller 315 also delivers intermittent pacing therapy in a stress augmentation mode.

When changed or switched from the normal operating mode to the stress augmentation mode, the pacing mode controller 315 delivers pacing therapy according to a second pacing mode and a third pacing mode. The second pacing mode and the third pacing mode increase mechanical stress on at least a particular portion of the ventricle as compared to the pacing therapy delivered during the first pacing mode. The pacing mode controller 315 alternates pacing therapy between the second and third pacing modes (e.g., between Pacing mode A and Pacing B in FIG. 2) when pacing is changed from the normal operating mode to a stress augmentation mode.

In some examples, the cardiac depolarization sensing circuit 305 is configured to obtain a sensed depolarization signal from an atrium such as by placement of an implantable electrode in or near the atrium, and the electrical stimulation circuit is configured to provide pacing electrical stimulation energy to the atrial electrode. In some examples, when in the normal or first operating mode, the pacing mode controller 315 provides the NASPE/BPEG-defined DDD pacing mode.

In some examples, when in the second pacing mode, the pacing mode controller 315 paces at least one ventricle (V), without timing the pacing of the ventricle from an atrial cardiac event, when a V-V interval exceeds a specified ventricular interval (e.g., the NASPE/BPEG-defined VVI pacing mode). In some examples, when in the third pacing mode, the pacing mode controller 315 paces an atrium and, in response to the pace in the atrium, triggers pacing of at least one ventricle after expiration of a specified fixed or dynamic AV delay without regard to any intrinsic cardiac depolarization event occurring in the ventricle (e.g., the NASPE/BPEG-defined DOO pacing mode).

The pacing mode controller 315 is configured to suspend a change from the normal operating mode to the stress augmentation mode when a condition to prevent the change is detected, and to retry the change to the stress augmentation mode. An example of a condition preventing the change to stress augmentation mode is atrial tachyarrhythmia response (ATR) pacing. In ATR pacing, the IMD 300 detects an atrial tachyarrhythmia and attempts to resolve the tachyarrhythmia by pacing the atrium. In some examples, the pacing mode controller 315 suspends the change to the stress augmentation mode when delivering ATR pacing therapy in the first pacing mode. In certain examples, the pacing mode controller 315 includes a timer circuit 320 and the pacing mode controller 315 retries the change to the stress augmentation mode a timed duration after the ATR pacing therapy. In certain examples, the pacing mode controller 315 retries the change from the normal operating mode to the stress augmentation mode when the condition preventing the change (e.g., the atrial tachyarrhythmia) is no longer detected.

According to some examples, the IMD 300 includes a preventing condition detector 330 communicatively coupled to the pacing mode controller 315 and the cardiac depolarization sensing circuit 305. The preventing condition detector 330 detects a condition that prevents the pacing mode controller 315 from initiating a change to the stress augmentation mode from the normal mode, or detects a condition that causes the pacing mode controller 315 to abort the stress augmentation mode. The pacing mode controller 315 may retry the change from the normal mode to the stress augmentation mode when the preventing condition is no longer present. In some examples, the pacing mode controller 315 includes a counter circuit 350. The pacing mode controller 315 is configured to retry the change from the normal operating mode to the stress augmentation mode for a programmable number of retry attempts before deactivating the stress augmentation mode.

In certain examples, the preventing condition detector 330 determines a heart rate using the sensed depolarization signal generated by the cardiac depolarization sensing circuit 305. The preventing condition detector 330 uses the depolarization signal to detect when the heart rate of a patient exceeds a heart rate threshold value. The pacing mode controller 315 suspends the change to the stress augmentation mode when the preventing condition detector detects the heart rate exceeds the heart rate threshold value. The heart rate threshold value may be set to detect patient exercise or to detect a tachyarrhythmia.

According to some examples, the IMD 300 includes a second electrical stimulation circuit 325 communicatively coupled to the pacing mode controller 315. In certain examples, the second electrical stimulation circuit 325 is an electrical high-energy shock stimulation circuit configured to provide at least one of cardioversion or defibrillation electrical stimulation energy to at least one implantable electrode. The pacing mode controller 315 suspends the change to the stress augmentation mode during delivery of the cardioversion or defibrillation electrical stimulation energy. In some examples, the pacing mode controller 315 retries the change from the normal operating mode to the stress augmentation mode a timed duration after delivery of the electrical high-energy shock stimulation energy.

In certain examples, the second electrical stimulation circuit 325 is an electrical neural stimulation circuit configured to provide electrical neural stimulation energy to at least one implantable electrode. The pacing mode controller 315 suspends the change to the stress augmentation mode during delivery of the electrical neural stimulation energy. In some examples, the pacing mode controller 315 retries the change from the normal operating mode to the stress augmentation mode a timed duration after delivery of the electrical neural stimulation energy.

Figure 4:
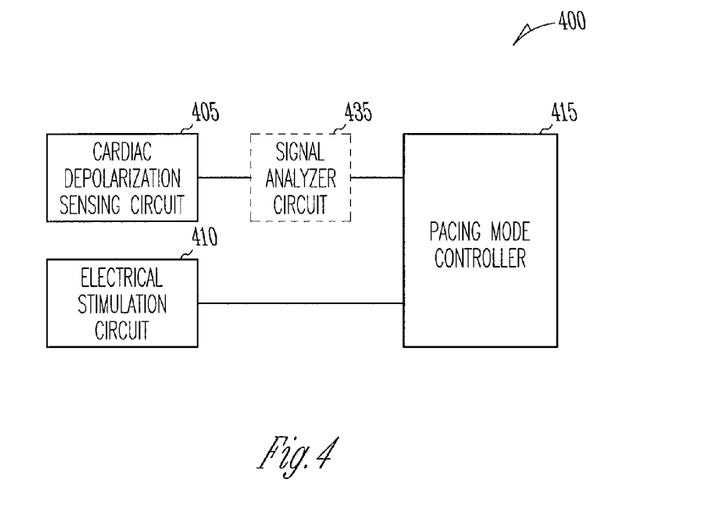
FIG. 4 is a block diagram of portions of another example of an IMD to provide intermittent pacing therapy in a stress augmentation mode.

FIG. 4 is a block diagram of portions of another example of an IMD 400 to provide intermittent pacing therapy in a stress augmentation mode. The IMD 400 includes at least one implantable cardiac depolarization sensing circuit 405, an electrical stimulation circuit 410, and a pacing mode controller 415. The pacing mode controller 415 delivers pacing therapy according to a normal mode and also delivers intermittent pacing therapy in a stress augmentation mode when pacing is changed from the normal operating mode.

The IMD 400 includes a signal analyzer circuit 435 communicatively coupled to the cardiac depolarization sensing circuit 405 and the pacing mode controller 415. The signal analyzer circuit 435 is configured to execute a scheduled measurement using a depolarization signal sensed by the cardiac depolarization sensing circuit 405. The pacing mode controller 415 suspends the change to the stress augmentation mode during the scheduled measurement. In some examples, the pacing mode controller 415 retries the change from the normal operating mode to the stress augmentation mode a timed duration after the scheduled measurement is completed. Examples of the scheduled measurement include, among other things, an amplitude measurement of an intrinsic depolarization signal sensed during the normal operating mode, or a time measurement of the depolarization signal, such as the time interval between a P-wave and R-wave of the depolarization signal. A P-wave in the depolarization signal is indicative of an atrial contraction and an R-wave is indicative of a ventricular contraction.

In some examples, the signal analyzer circuit 435 executes a diagnostic measurement using the sensed depolarization signal. The pacing mode controller 415 suspends the change to the stress augmentation mode during the diagnostic measurement. The pacing mode controller 415 may retry the change from the normal operating mode to the stress augmentation mode a timed duration after the scheduled measurement is completed. Examples of a diagnostic measurement include diagnostic measurements to assess heart signal stability. Examples of a diagnostic measurement to classify the sensed signal include a measure of rhythm stability or a morphology comparison. Examples of systems and methods to detect abnormal heart rhythms and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety. Examples of systems and methods of creating templates for a morphology-based algorithm are described in Hsu, U.S. Pat. No. 6,889,081, entitled "Classification of Supra-ventricular and Ventricular Cardiac Rhythms Using Cross Channel Timing Algorithm," filed Jul. 23, 2002, which is incorporated herein by reference in its entirety.

In some examples, the signal analyzer circuit 435 detects electrical energy being supplied by a second device separate from the implantable device to perform a diagnostic measurement. The second device may be a separate implantable device or an external device. Examples include, among other things, instruments to acquire an electrocardiogram, an electroencephalogram, an electromyogram, thoracic impedance, or cardiac impedance. The signal analyzer circuit 435 detects, using the sensed depolarization signal, electrical energy applied by a second separate device as part of a diagnostic measurement. The pacing mode controller 415 is suspends the change to the stress augmentation mode when the preventing condition detector detects the applied electrical energy. The pacing mode controller 415 may retry the change from the normal mode to the stress augmentation mode when the electrical energy is no longer detected.

Figure 5:
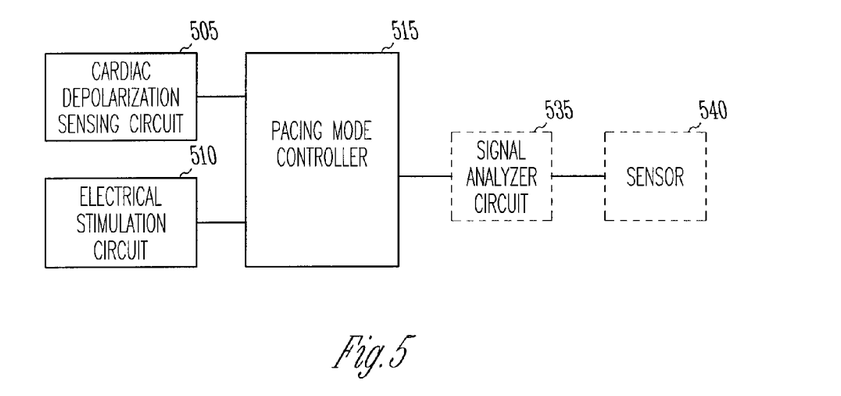
FIG. 5 is a block diagram of portions of yet another example of an IMD to provide intermittent pacing therapy in a stress augmentation mode.

According to some examples, the signal analyzer circuit 435 executes a diagnostic measurement using a sensor circuit different from the cardiac depolarization sensing circuit 405. FIG. 5 is a block diagram of portions of another example of an IMD 500 to provide intermittent pacing therapy in a stress augmentation mode. The IMD 500 includes an implantable cardiac depolarization sensing circuit 505, an electrical stimulation circuit 510, and a pacing mode controller 515. The pacing mode controller 515 delivers pacing therapy according to a stress augmentation mode when pacing is changed from a normal operating mode.

The IMD 500 also includes a sensor circuit 540 to generate an electrical sensor signal related to one or more physiologic cardiovascular events in the patient. The IMD 500 may also include a signal analyzer circuit 535 communicatively coupled to the sensor circuit 540. The signal analyzer circuit 535 executes a diagnostic measurement using the electrical sensor signal and the pacing mode controller 515 suspends the change to the stress augmentation mode during the diagnostic measurement.

In some examples, the sensor circuit 540 is an implantable impedance sensor circuit configured to provide a sensed cardiac impedance signal. In certain examples, the implantable impedance sensor circuit provides a signal representative of transthoracic impedance of the patient or subject. In an illustrative example, in FIG. 1 a transthoracic impedance of a subject can be measured by delivering a predetermined excitation current between the ring electrode 120B and an electrode formed on the can of IMD 105 and determining the impedance from the voltage sensed between the electrodes.

The signal analyzer circuit 535 executes a diagnostic measurement using the transthoracic impedance signal, such as determining a minute respiration volume for example. An approach to measuring transthoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference.

In certain examples, the implantable impedance sensor circuit provides a signal representative of intracardiac impedance of the patient or subject. Electrodes placed within the right ventricle of the heart provide a signal of intracardiac impedance versus time. The signal analyzer circuit 535 processes the intracardiac impedance signal to obtain a diagnostic measurement. For example, the signal analyzer circuit 535 may measure a time interval beginning with a paced or spontaneous QRS complex (systole marker) and ending with a point where the impedance signal crosses the zero axis in the positive direction following the QRS complex. The resulting time interval is inversely proportional to the contractility of the heart. Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference in its entirety.

Figure 6:
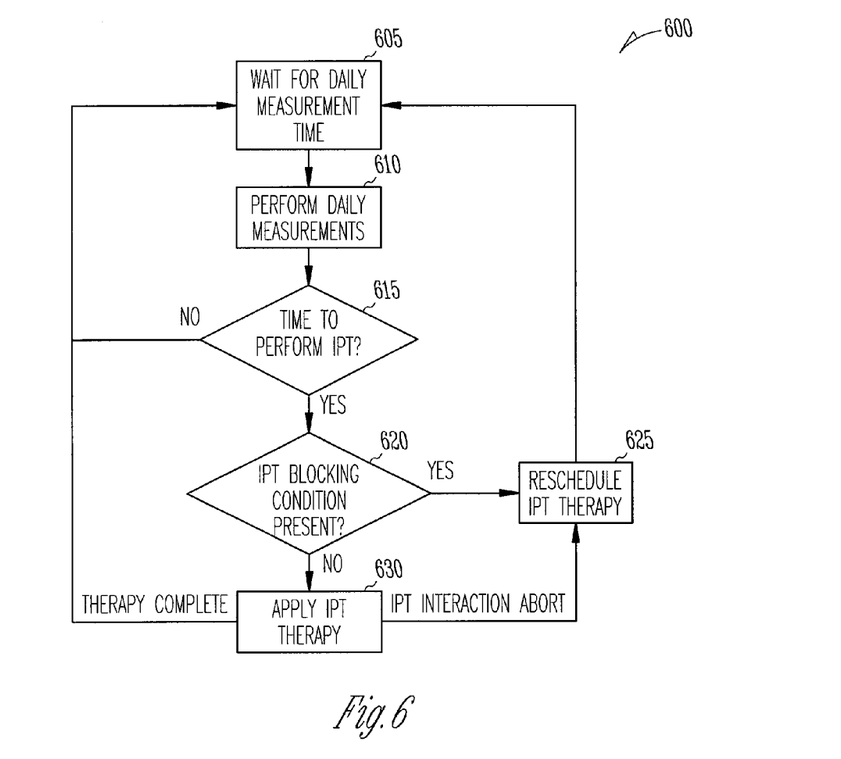
FIG. 6 is a flow diagram of an example of a method of providing intermittent pacing therapy in a stress augmentation mode using an implantable device.

FIG. 6 is a flow diagram of an example of a method 600 of providing intermittent pacing therapy (IPT) in a stress augmentation mode using an implantable device. At block 605, the implantable device waits for a recurrent time to take one or more measurements. In the example, the implantable device takes the measurements daily. Examples of measurements include the various examples of scheduled and diagnostic measurements described herein. At block 610, the implantable device performs the scheduled measurement.

At block 615, the implantable device determines whether it is a scheduled time for pacing according to IPT to be delivered. If not, the implantable device waits to complete the next scheduled measurement at block 605. If it is time to deliver IPT, the implantable device determines whether a condition to prevent or block a change from normal mode to IPT is present at block 620. If a preventing condition is present, the implantable device delays IPT and reschedules the IPT session at block 625.

At block 630, if a preventing condition is not present, the implantable device applies IPT therapy. If a preventing condition develops, the implantable device may abort the IPT session which is rescheduled at block 625. If no preventing condition develops, the implantable device completes the IPT session and waits at block 605 to perform the next scheduled measurement.

Returning to FIG. 5, in some examples, the sensor circuit 540 is a magnetic field sensor circuit. The pacing mode controller 515 suspends the change to the stress augmentation mode when the magnetic field sensor circuit detects a magnetic field. In certain examples, the pacing mode controller 515 retries the change to the stress augmentation mode from the normal mode when the magnetic field is no longer detected.

Figure 7:
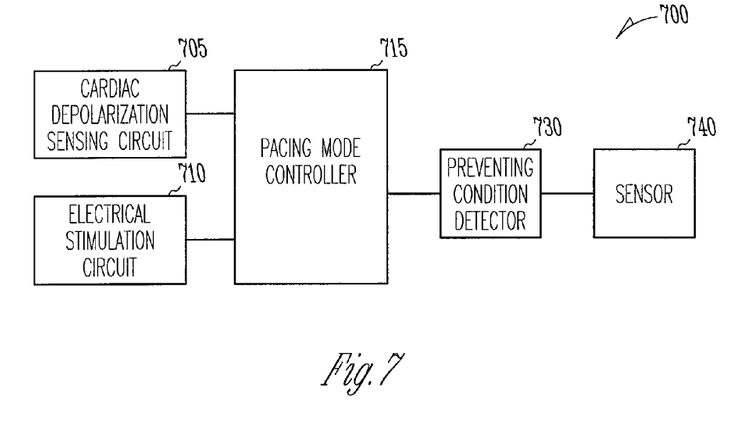
FIG. 7 is a block diagram of portions of another example of an IMD to provide intermittent pacing therapy in a stress augmentation mode.

FIG. 7 is a block diagram of portions of another example of an IMD 700 to provide intermittent pacing therapy in a stress augmentation mode. The IMD 700 includes an implantable cardiac depolarization sensing circuit 705, an electrical stimulation circuit 710, and a pacing mode controller 715. The pacing mode controller 715 delivers pacing therapy according to a stress augmentation mode when pacing is changed from a normal operating mode. The IMD 700 includes a preventing condition detector 730. The preventing condition detector 730 detects a condition that prevents the pacing mode controller 715 from initiating a change to the stress augmentation mode from the normal mode, or detects a condition that causes the pacing mode controller 715 to abort the stress augmentation mode.

The preventing condition detector 730 is communicatively coupled to sensor circuit 740. In some examples, the sensor circuit 740 includes an activity sensor circuit that produces an activity sensor signal representative of activity of a patient. An example of an implantable patient activity sensor is an accelerometer. The preventing condition detector 730 detects from the activity sensor signal when the patient exceeds an activity level threshold value. The pacing mode controller 715 suspends the change to the stress augmentation mode when the activity level of the patient exceeds the activity level threshold value. In certain examples, the pacing mode controller 715 retries the change to the stress augmentation mode when the activity level of the patient decreases below the same activity level threshold value or a different activity level threshold value. This provides some hysteresis regarding activity level when changing to the stress augmentation mode.

In some examples, the sensor circuit 740 includes a respiration sensor circuit. The respiration sensor circuit produces a respiration sensor signal representative of respiration of a patient. An example of an implantable respiration sensor is a transthoracic impedance sensor to measure minute respiration volume. An approach to measuring transthoracic impedance is described in the above mentioned U.S. Pat. No. 6,076,015. The preventing condition detector 730 detects from the respiration sensor signal an episode of at least one of apnea, hypopnea, or hyperventilation. The pacing mode controller 715 suspends the change to the stress augmentation mode during the episode. In certain examples, the pacing mode controller 715 retries the change to the stress augmentation mode when the episode is no longer present.

Figure 8:
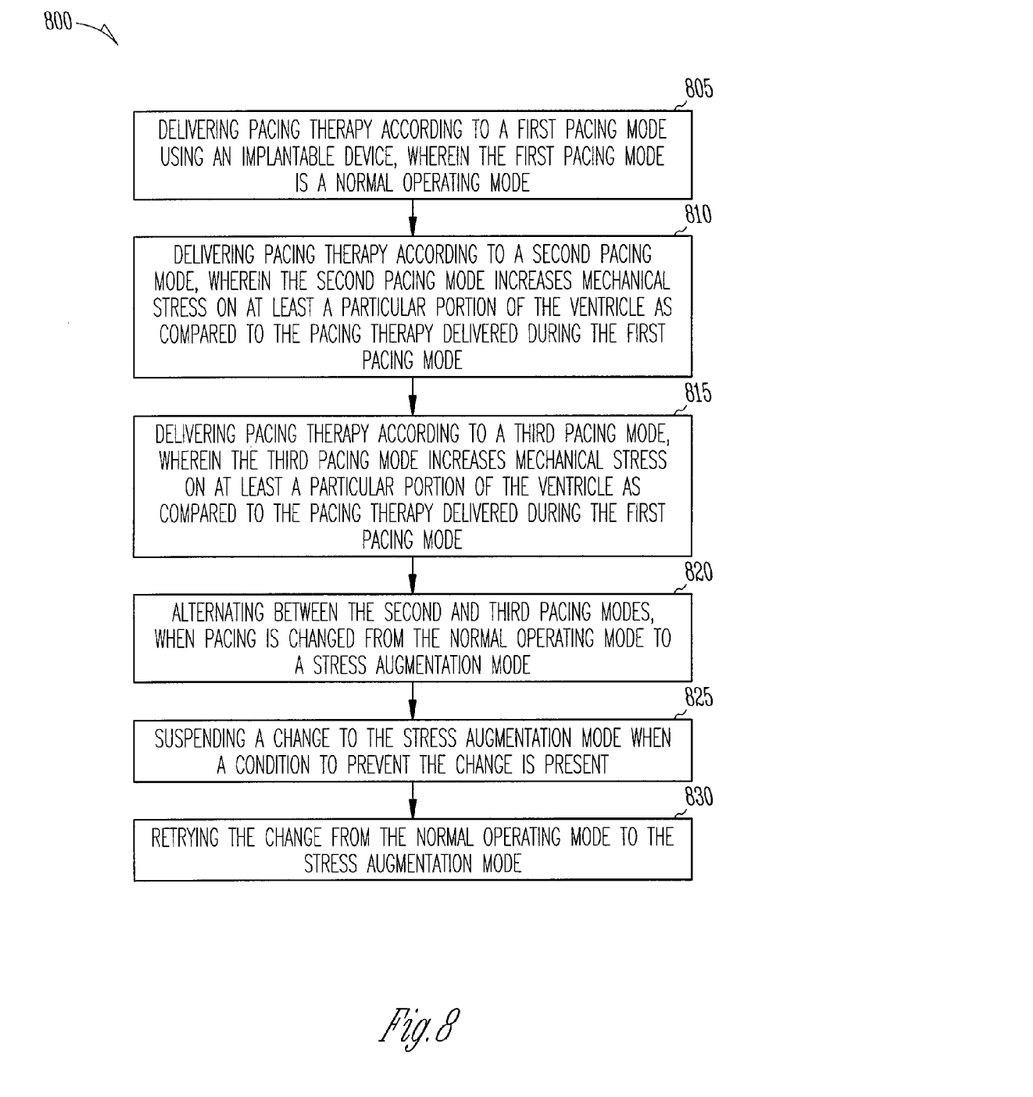
FIG. 8 is a flow diagram of another example of a method of providing intermittent pacing therapy in a stress augmentation mode using an implantable device.

FIG. 8 is a flow diagram of an example of a method 800 of providing intermittent pacing therapy in a stress augmentation mode using an implantable device. At block 805, pacing therapy is delivered according to a first pacing mode using an implantable device. The first pacing mode is a normal operating mode.

At block 810, pacing therapy is delivered according to a second pacing mode using the implantable device. The second pacing mode increases mechanical stress on at least a particular portion of the ventricle as compared to the pacing therapy delivered during the first pacing mode. At block 815, pacing therapy is delivered according to a third pacing mode that increases mechanical stress on at least a particular portion of the ventricle as compared to the pacing therapy delivered during the first pacing mode. In certain examples, the mechanical stress of the second and third pacing modes is due to an increase in ventricular dyssynchrony caused by the second and third pacing modes. The second and third pacing modes are included in a stress augmentation mode.

At block 820, the implantable device alternates between the second and third pacing modes when pacing is changed from the normal operating mode to a stress augmentation mode.

At block 825, the change to the stress augmentation is suspended when a condition to prevent the change is present.

This can be viewed as a safety shut-off for the stress augmentation mode. The preventing condition may be a condition that prevents initiation of a change to the stress augmentation mode from the normal mode, or a condition that causes the stress augmentation mode to be aborted.

In some examples, the preventing condition is delivery of a different higher priority therapy than the intermittent pacing therapy of the stress augmentation mode. A non-exhaustive list of examples of delivering a higher priority therapy include delivering pacing therapy according to an atrial tachyarrhythmia response in the first pacing mode, delivering defibrillation therapy, delivering cardioversion therapy, or delivering neural stimulation therapy.

In some examples, the condition that prevents the change includes the implantable device detecting that the patient is exercising. It may not be desirable to pace according to the stress augmentation mode when the patient's heart rate is elevated during exercise. In some examples, the preventing condition includes the implantable device detecting an indication of a specified breathing episode of the patient. Examples of the indication include, among other things, an indication of apnea, hypopnea, or hyperventilation.

At block 830, the implantable device retries the change from the normal operating mode to the stress augmentation mode. In some examples, the implantable retries the change a programmable time duration after the change was suspended. In some examples, the implantable device retries the change from the normal operating mode to the stress augmentation mode for a programmable number of retry attempts before deactivating the stress augmentation mode. In some examples, the implantable device retries the change from the normal operating mode to the stress augmentation mode after the implantable device determines the condition to prevent the change is no longer present.

As discussed previously, providing intermittent regional stress may halt progression of ventricular dilatation. As described in the several examples herein, the intermittent pacing therapy sessions may by delayed, aborted or modified due to conditions of the patient or due to conditions of the implantable device. A session or sessions may also be delayed, aborted or modified by programming the implantable device with an external device. The external device may modify any of the delivery parameters of an intermittent pacing therapy session.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   at least one implantable cardiac depolarization sensing circuit configured to provide a sensed depolarization signal from a ventricle;
   an electrical stimulation circuit configured to provide pacing electrical stimulation energy to at least one implantable electrode in the ventricle; and
   a pacing mode controller communicatively coupled to the cardiac depolarization sensing circuit and the electrical stimulation circuit, wherein the pacing mode controller is configured to:
     deliver pacing therapy according to a first pacing mode, wherein the first pacing mode is included in a normal operating mode;
     deliver pacing therapy according to a second pacing mode, wherein the second pacing mode senses intrinsic cardiac events differently than in the first pacing mode, triggers or inhibits delivery of pacing pulses according to intrinsic cardiac events differently than in the first pacing mode, and increases mechanical stress on at least a particular portion of the ventricle as compared to the pacing therapy delivered during the first pacing mode;

deliver pacing therapy according to a third pacing mode different from the second pacing mode, wherein the third pacing mode senses intrinsic cardiac events differently than in the first pacing mode, triggers or inhibits delivery of pacing pulses according to intrinsic cardiac events differently than in the first pacing mode or the second pacing mode, and increases mechanical stress on at least a particular portion of the ventricle as compared to the pacing therapy delivered during the first pacing mode;

alternate between the second and third pacing modes when pacing is changed from the normal operating mode to a stress augmentation mode; and suspend a change from the normal operating mode to the stress augmentation mode when a condition to prevent the change is detected.

2. The apparatus of claim 1, wherein the pacing mode controller is configured to retry the change to the stress augmentation mode after suspending the change from the normal operating mode.

3. The apparatus of claim 2, wherein the pacing mode controller includes a timer circuit, and wherein the pacing mode controller is configured to retry the change from the normal operating mode to the stress augmentation mode after a programmable time duration.

4. The apparatus of claim 2, wherein the pacing mode controller includes a counter circuit, and wherein the pacing mode controller is configured to retry the change from the normal operating mode to the stress augmentation mode for a programmable number of retry attempts before deactivating the stress augmentation mode.

5. The apparatus of claim 2, wherein the pacing mode controller is configured to retry the change from the normal operating mode to the stress augmentation mode when the condition to prevent the change is no longer detected.

6. The apparatus of claim 1, wherein the pacing mode controller is configured to suspend the change to the stress augmentation mode when delivering atrial tachyarrhythmia response pacing therapy in the first pacing mode.

7. The apparatus of claim 1, including:
an electrical high-energy shock stimulation circuit, communicatively coupled to the pacing mode controller, configured to provide at least one of cardioversion or defibrillation electrical stimulation energy to at least one implantable electrode; and
wherein the pacing mode controller is configured to suspend the change to the stress augmentation mode during delivery of the cardioversion or defibrillation electrical stimulation energy.

8. The apparatus of claim 1, including:
an electrical neural stimulation circuit, communicatively coupled to the pacing mode controller, configured to provide electrical neural stimulation energy to at least one implantable electrode; and
wherein the pacing mode controller is configured to suspend the change to the stress augmentation mode during delivery of the electrical neural stimulation energy.

9. The apparatus of claim 1, including:
a preventing condition detector, communicatively coupled to the pacing mode controller and the cardiac depolarization sensing circuit, configured to determine a heart rate using the sensed depolarization signal and to detect when the heart rate of a patient exceeds a heart rate threshold value; and wherein the pacing mode controller is configured to suspend the change to the stress augmentation mode when the preventing condition detector detects the heart rate exceeds the heart rate threshold value.

10. The apparatus of claim 1, including:
an activity sensor circuit to produce an activity sensor signal representative of activity of a patient;
a preventing condition detector, communicatively coupled to the pacing mode controller and the activity sensor circuit, configured to detect from the activity sensor signal when an activity level of the patient exceeds an activity level threshold value; and
wherein the pacing mode controller is configured to suspend the change to the stress augmentation mode when the activity level of the patient exceeds the activity level threshold value.

11. The apparatus of claim 1, including:
a signal analyzer circuit communicatively coupled to the cardiac depolarization sensing circuit, wherein the signal analyzer circuit is configured to execute a scheduled measurement using the sensed depolarization signal; and
wherein the pacing mode controller is configured to suspend the change to the stress augmentation mode during the scheduled measurement.

12. The apparatus of claim 1, including:
a signal analyzer circuit communicatively coupled to the cardiac depolarization sensing circuit, wherein the signal analyzer circuit is configured to execute a diagnostic measurement using the sensed depolarization signal; and
wherein the pacing mode controller is configured to suspend the change to the stress augmentation mode during the diagnostic measurement.

13. The apparatus of claim 1, including:
an implantable impedance sensor circuit configured to provide a sensed cardiac impedance signal;
a signal analyzer circuit communicatively coupled to the impedance sensor circuit, wherein the signal analyzer circuit is configured to execute a diagnostic measurement using the cardiac impedance signal; and
wherein the pacing mode controller is configured to suspend the change to the stress augmentation mode during the diagnostic measurement.

14. The apparatus of claim 1, including:
a signal analyzer circuit communicatively coupled to the pacing mode controller and the cardiac depolarization sensing circuit, wherein the signal analyzer circuit is configured to detect, using the sensed depolarization signal, electrical energy applied by a second separate device as part of a diagnostic measurement; and
wherein the pacing mode controller is configured to suspend the change to the stress augmentation mode when the preventing condition detector detects the applied electrical energy.

15. The apparatus of claim 1, including:
a magnetic field sensor circuit communicatively coupled to the pacing mode controller, and
wherein the pacing mode controller is configured to suspend the change to the stress augmentation mode when the magnetic field sensor circuit detects a magnetic field.

16. The apparatus of claim 1, including:
a respiration sensor circuit configured to produce a respiration sensor signal representative of respiration of a patient;
a preventing condition detector communicatively coupled to the pacing mode controller and the respiration sensor circuit, wherein the preventing condition detector is configured to detect, using the respiration sensor signal, an episode of at least one of apnea, hypopnea, or hyperventilation; and wherein the pacing mode controller is configured to suspend the change to the stress augmentation mode during the episode.

17. A method comprising:
delivering pacing therapy according to a first pacing mode using an implantable device, wherein the first pacing mode is included in a normal operating mode;
delivering pacing therapy according to a second pacing mode, wherein the second pacing mode senses intrinsic cardiac events differently than in the first pacing mode, triggers or inhibits delivery of pacing pulses according to intrinsic cardiac events differently than in the first pacing mode, and increases mechanical stress on at least a particular portion of the ventricle as compared to the pacing therapy delivered during the first pacing mode;
delivering pacing therapy according to a third pacing mode different from the second pacing mode, wherein the third pacing mode senses intrinsic cardiac events differently than in the first pacing mode, triggers or inhibits delivery of pacing pulses according to intrinsic cardiac events differently than in the first pacing mode or the second pacing mode, and increases mechanical stress on at least a particular portion of the ventricle as compared to the pacing therapy delivered during the first pacing mode;
alternating between the second and third pacing modes, when pacing is changed from the normal operating mode to a stress augmentation mode; and
suspending a change to the stress augmentation mode when a condition to prevent the change is present.

18. The method of claim 17, including retrying the change from the normal operating mode to the stress augmentation mode after suspending the change to the stress augmentation mode.

19. The method of claim 18, wherein retrying includes retrying the change from the normal operating mode to the stress augmentation mode after a programmable time duration.

20. The method of claim 18, wherein retrying includes retrying the change from the normal operating mode to the stress augmentation mode for a programmable number of retry attempts before deactivating the stress augmentation mode.

21. The method of claim 18, wherein retrying includes retrying the change from the normal operating mode to the stress augmentation mode after the implantable device determines the condition to prevent the change is no longer present.

22. The method of claim 17, wherein suspending a change to the stress augmentation mode includes suspending the change during delivery of a different higher priority therapy.

23. The method of claim 22, wherein the higher priority therapy includes at least one of:
delivering pacing therapy according to an atrial tachyarrhythmia response in the first pacing mode;
delivering defibrillation therapy;
delivering cardioversion therapy; or
delivering neural stimulation therapy.

24. The method of claim 17, wherein suspending a change to the stress augmentation mode includes suspending the change to the stress augmentation mode when the implantable device detects a patient is exercising.

25. The method of claim 17, wherein suspending a change to the stress augmentation mode includes suspending a change to the stress augmentation mode until after a scheduled measurement is completed by the implantable device.

26. The method of claim 17, wherein suspending a change to the stress augmentation mode includes suspending the change when the implantable device determines a patient diagnostic measurement is being made.

27. The method of claim 17, wherein suspending a change to the stress augmentation mode includes suspending the change to the stress augmentation mode when the implantable device detects a presence of a magnetic field.

28. The method of claim 17, wherein suspending a change to the stress augmentation mode includes suspending the change to the stress augmentation mode when the implantable device detects an indication of at least one of:
apnea;
hypopnea; or
hyperventilation.

* * * * *